United States Patent [19]

Taylor

[11] Patent Number: 5,405,742
[45] Date of Patent: Apr. 11, 1995

[54] SOLUTIONS FOR TISSUE PRESERVATION AND BLOODLESS SURGERY AND METHODS USING SAME

[75] Inventor: Michael J. Taylor, Pittsburgh, Pa.

[73] Assignee: Cryomedical Sciences, Inc., Rockville, Md.

[21] Appl. No.: 92,456

[22] Filed: Jul. 16, 1993

[51] Int. Cl.$^6$ ............. A01N 1/02; A61M 37/00
[52] U.S. Cl. ........................... 435/1; 604/4; 514/832
[58] Field of Search ............ 435/1, 2; 604/4; 514/832

[56] References Cited

U.S. PATENT DOCUMENTS

| | | | |
|---|---|---|---|
| 4,920,044 | 4/1990 | Bretan, Jr. ................ | 435/1 |
| 4,923,442 | 5/1990 | Segall et al. ............... | 604/52 |
| 5,082,831 | 1/1992 | Leaf et al. ................. | 514/56 |
| 5,290,766 | 3/1994 | Choong ...................... | 514/23 |
| 5,306,711 | 4/1994 | Andrews .................... | 514/59 |

OTHER PUBLICATIONS

Ely D et al, Free Radic Biol Med 12(6): 479–85 (1992).
Menashe P, et al, J. Thorac Cardiovasc Surg. 100(1): 13–21 (1990).

Primary Examiner—Douglas W. Robinson
Assistant Examiner—Sandra Saucier
Attorney, Agent, or Firm—Sherman and Shalloway

[57] ABSTRACT

A solution suitable as a hypothermic blood substitute for replacing blood in euthermic subjects during surgery are provided. The blood substitute contains a purge solution and a maintenance solution, the latter of which is useful for organ preservation. The purge solution contains an aqueous solution of electrolytes at physiological concentrations, a macromolecular oncotic agent, a biological pH buffer effective under physiological and hypothermic conditions, a simple sugar, and a substrate for the regeneration of ATP. The maintenance solution contains a second aqueous solution of electrolytes containing potassium ions at a concentration range of from 35 to 45 mM, sodium ions at a concentration range of from 80 to 120 mM, magnesium ions at a concentration range of from 2 to 10 mM, chloride ions at a concentration range of from 15 to 20 mM, and calcium ions at a concentration range of from 0.01 to 0.1 mM, an impermeant anion, mannitol, a macromolecular oncotic agent, at least one simple sugar, a substrate for the regeneration of ATP, and a biological pH buffer effective under physiological hypothermic conditions pH. Glutathione is an optional but preferred additive. The blood substitute solutions are also useful for preserving organs for later transplantation in subjects. Skin may be preserved in the maintenance solutions for extended periods under refrigeration.

19 Claims, 5 Drawing Sheets

SOLUTIONS FOR TISSUE PRESERVATION AND BLOODLESS SURGERY AND METHODS USING SAME

FIELD OF THE INVENTION

The present invention relates to blood-substitute solutions. In particular it relates to blood-substitute solutions useful during controlled whole body hypothermia and flush and storage solutions for preserving tissues for transplantation or grafting, including purging the tissues prior to reperfusion. The present invention also relates to the method for preserving tissues using the flush and storage solution and to the method for performing bloodless hypothermic procedures on living subjects.

BACKGROUND OF THE INVENTION

Recent advances in surgical methods and the development of blood substitutes have permitted surgeons to carry out extremely time-consuming and complicated surgical procedures in which the subject's body temperature is lowered to minimize damage to the subject's brain and vital organs. Lowering the temperature of an euthermic subject to a temperature well below that normally homeostatically maintained by the subject reduces the metabolic rate, which in course, decreases the demands for oxygen and glucose of the vital tissues and organs. This is particularly important for carrying out procedures on the organs of the central nervous system, which require large amounts of glucose and oxygen. Consequently, while time-consuming and complicated procedures, such as neurosurgery and cardiovascular procedures can be carried out, however, time constraints are still an important factor in such procedures.

A number of blood substitutes have been developed in the past. These blood substitutes have been used primarily as hypothermic preservation solutions for transplantable organs and tissues, which are surgically removed from donors to be later transplanted. The majority of blood substitutes used in organ preservation are solutions of substances that readily permeate the vasculature of the subject's or donor's organs and consequently, are not very useful in surgery on living subjects. Examples of blood substitutes containing primarily vasculature permeable substances include the blood substitutes of Collins, et al., Lancet 1219–1222 (1969), Collins G. M., Transplant. Proc. IX. 1529 (1977), Fischer, et al., Transplantation 21:498 (1976), Sacks, et al., Transplantation 19:283 (1974), Kallerhoff, et al., Transplantation, 39:5, 485–489 (1985) and Klebanoff and Phillips, Cryobiology, 6:121–125 (1969). Each of these blood substitutes contain only low molecular weight molecules, which are capable of passing through the vasculature of the subject and consequently, are ineffective at maintaining proper ionic or fluid balance or plasma volume for extended periods of time.

Wall, et al. disclose blood substitutes useful for cryostatic preservation of organs and tissues for implantations containing human serum albumin as an impermeable substance to maintain volume. (Transplantation 23:210 (1977)). This plasma-based blood substitute requires the processing of human blood and consequently, exposes subjects to the risk of infection by blood transmitted diseases, such as hepatitis A, B or non-A-non-B virus or the AIDS virus. Clearly it is desirable to use non-blood based blood substitutes.

Non-blood based blood substitutes useful for preserving organs and tissues for transplant are disclosed by Breton, Jr. (U.S. Pat. No. 4,920,044) and Belzer, et al. (U.S. Pat. No. 4,879,283 and U.S. Pat. No. 4,798,824). Breton, Jr.'s hyperosmotic intracellular organ flush and maintenance solutions contain neither colloids for oncotic support nor lactobionate to maintain cellular anion and hydraulic balance. Belzer's solutions for organ preservation contain impermeants and colloids for osmotic support, however, patentees' solution contains concentrations of potassium ions and sodium ions of 120 mM and 30 mM, respectively. These concentrations of ions are within the range of normal intracellular values and consequently, passive diffusional loss of cellular potassium and gain of sodium are inhibited or compensated for. These ionic concentrations are not applicable to whole body hypothermic blood substitutes in view of evidence that high potassium levels induce necrosis in myocardial tissue (contraction-band necrosis). Also, much lower potassium levels (e.g. less than 10 mM) are needed in order to reactivate the heart during rewarming.

Solutions used as blood substitutes for surgery on living subjects are formulated with different criteria than those blood substitute solutions used in organ preservation. For example, during protracted surgical procedures it is essential to maintain body fluid balance between the subject's vasculature and interstitial spaces of the cells. It is also necessary to maintain the subject's blood pH during surgery. Segall, et al. (U.S. Pat. No. 4,923,422) disclose a four-solution blood substitute useful in hypothermic preservation of isolated organs for use in transplantations, as well as in bloodless surgery using whole body hypothermia. Patentees disclose blood substitute solutions containing varying levels of dextrose depending on the surgical procedure for which the blood substitute is used. However, patentees specifically note that use of mannitol is to be avoided when the blood substitute is administered to living subjects because use of this sugar is associated with significant decreases in pH that are usually uncontrollable even with dialysis. Patentees disclose that recovery of a subject that had been perfused with the four solution blood substitute was slow, with the animal unable to stand for the first post-operative month.

Clearly, a blood substitute that provides the benefits of prolonged preservation time as required by organ storage preservation solutions and which protects the brain and visceral organs during controlled hypothermia is desired. Major benefits for protracted surgical procedures such as certain neurosurgical and cardiovascular procedures would be realized if the time constraints of approximately one hour, imposed by present technologies for cardiac arrest during hypothermia could be extended without significant ischemic injury. Moreover, it is also desired that recovery of the subject after bloodless surgery be very fast.

SUMMARY OF THE INVENTION

Figure 1:
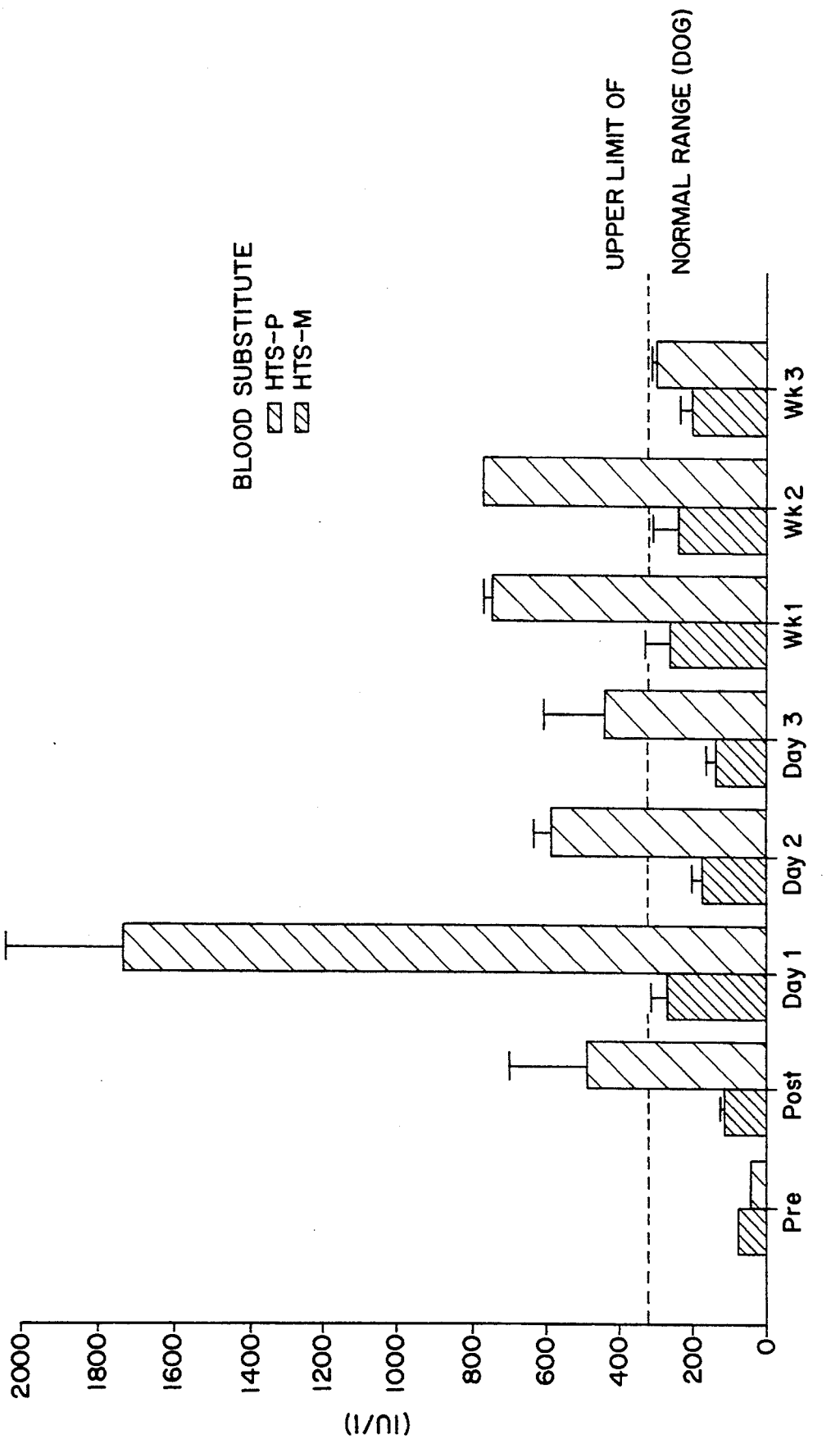
FIG. 1 is a bar graph of the levels of lactate dehydrogenase (LDH) in animals perfused with maintenance solution and purged with purge solution (experimental HTS/P+HTS/M) and animals that were only perfused with purge solution (control HTS-P).
Figure 2A:
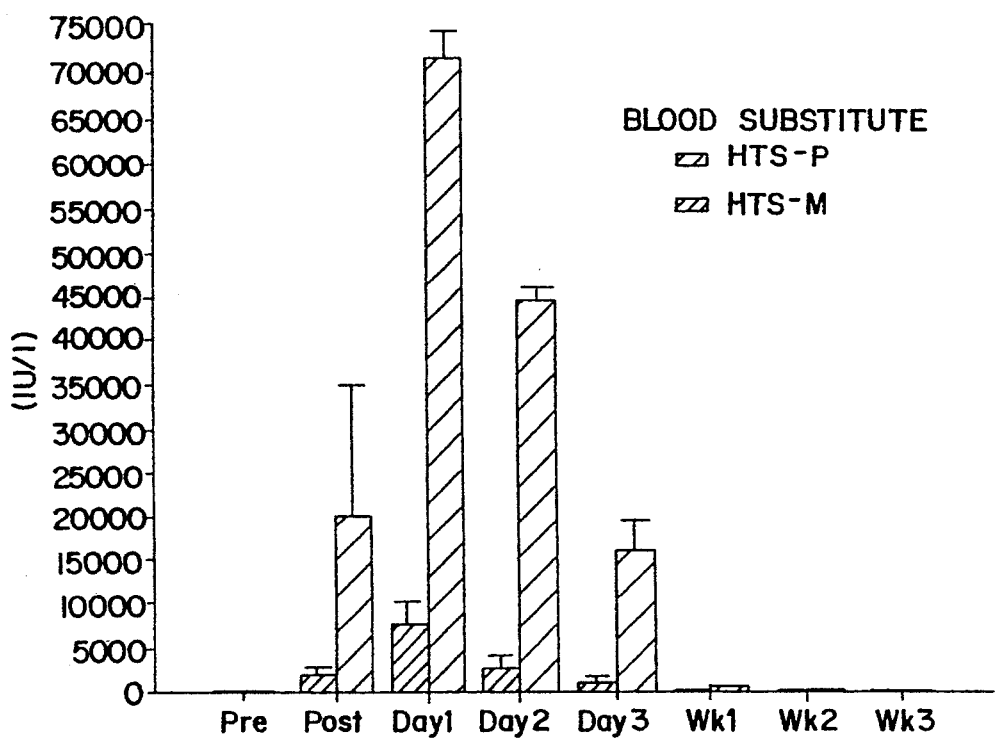
FIG. 2(a) is a bar graph of serum levels of creatine kinase (CK) and its isozymes in experimental (HTS-P/HTS-M) and control (HTS-P) animals.
Figure 2B:
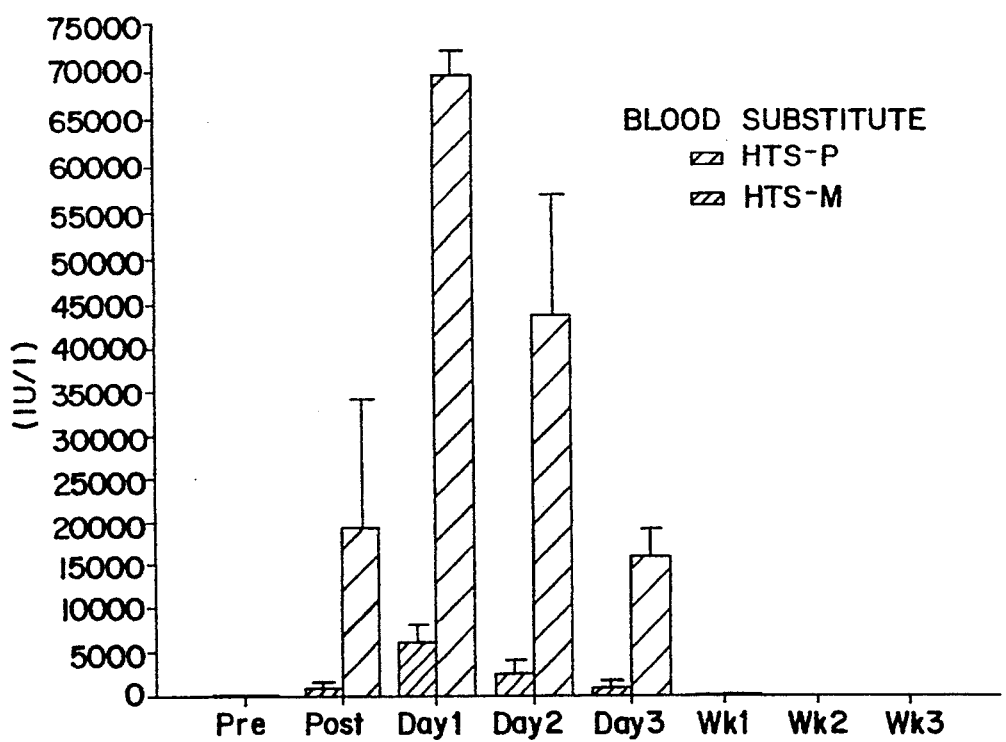
FIG. 2(b) is a bar graph of serum CK levels derived from skeletal muscle of experimental (HTS-P/HTS-M) and control (HTS-P) animals.
Figure 2C:
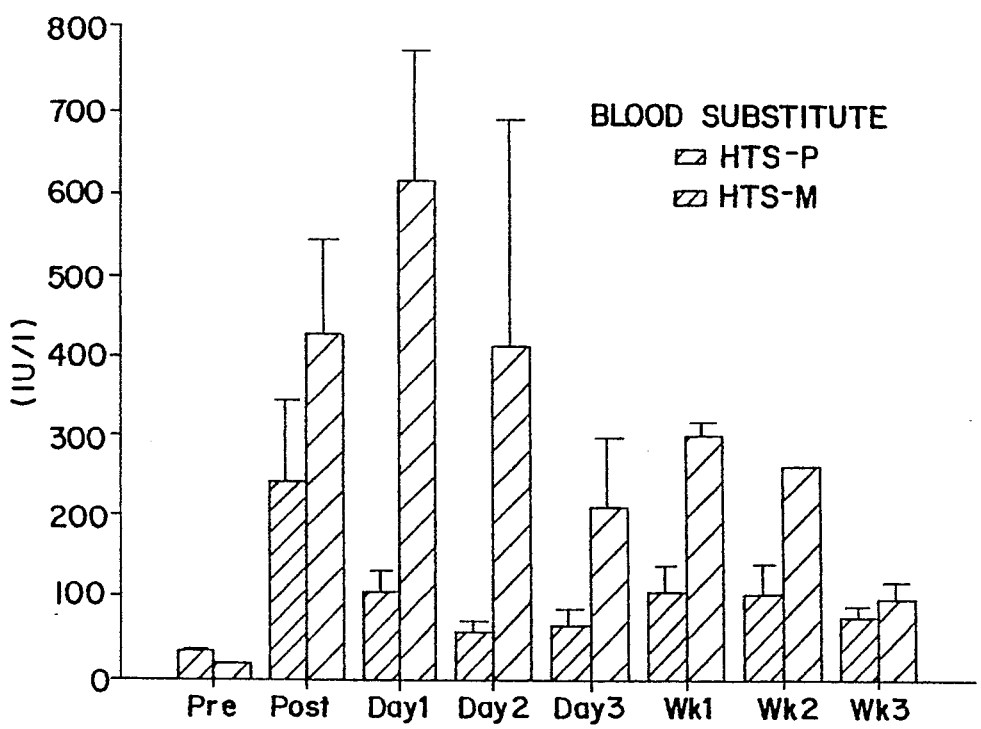
FIG. 2(c) is a bar graph of serum CK levels derived from brain tissue of experimental (HTS-P/HTS-M) and control (HTS-P) animals.
Figure 2D:
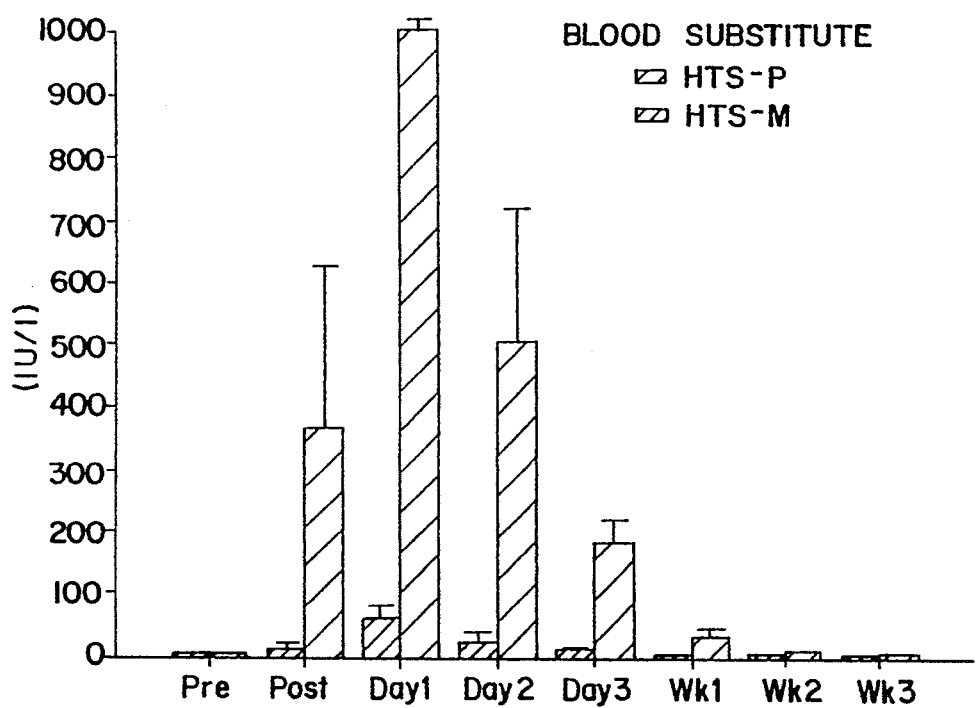
FIG. 2(d) is a bar graph of serum CK levels derived from heart-tissue of experimental (HTS-P/HTS-M) and control (HTS-P) animals.

The present invention provides a cell-free hypothermic blood substitute, which is also useful as a solution for the maintenance and preservation of tissues intended for transplantation in a patient, containing (1) an aqueous solution of electrolytes including potassium ions at a concentration range of from 35 to 45 millimoles/liter (mM), sodium ions at a concentration range of from 80 to 120 millimoles/liter (mM), magnesium ions at a concentration range of from 2 to 10 mM, and calcium ions at a concentration range of from 0.01 to 0.1 mM, (2) a macromolecular oncotic agent, (3) a biological pH buffer effective under physiological and hypothermic conditions, (4) at least one simple sugar, (5) mannitol, (6) an impermeant anion, and (7) a substrate for the regeneration of ATP and, optionally, (8) glutathione.

In a preferred embodiment of the invention the macromolecular oncotic agent is an impermeant polysaccharide. In particular, the preferred impermeant polysaccharides include Dextran 40 and Dextran 70. The preferred substrate for regeneration of ATP is adenosine.

In yet another preferred embodiment the solution also contains an inhibitor of xanthine oxidase and a 5′nucleotidase inhibitor. In another preferred embodiment the solution further contains an iron-chelating agent. In still another preferred embodiment the solution includes a membrane channel blocker, e.g. fast channel blocker or calcium channel blocker. In a further preferred embodiment of the invention the impermeant anion is a lactobionate salt, preferably in a concentration of about 100 mM. In another preferred embodiment the solution contains buffering amounts of $H_2PO_4^-$ and $HCO_3^-$.

In another aspect of the invention, there is provided a two-solution cell-free blood substitute capable of maintaining a subject and its organs at temperatures below 20° C. The blood substitute includes (A) a purge solution and (B) a maintenance solution. Purge solution (A) is an aqueous solution (first aqueous solution) of electrolytes at about physiological concentrations, a macromolecular oncotic agent, a biological pH buffer effective at physiological and reduced temperatures, a simple sugar, and a substrate for the regeneration of ATP. Maintenance solution (B) corresponds to the cell-free hypothermic blood substitute described above and contains (1) an aqueous solution (second aqueous solution) of electrolytes containing potassium ions at a concentration range of from 35 to 45 mM, sodium ions at a concentration range of from 80 to 120 mM, magnesium ions at a concentration range of from 2 to 10 mM, chloride ions at a concentration range of from 15 to 20 mM, and calcium ions at a concentration range of from 0.01 to 0.1 mM, (2) an impermeant anion, (3) mannitol, (4) a macromolecular oncotic agent, (5) at least one simple sugar, (6) a substrate for the regeneration of ATP, and (7) a biological pH buffer effective under physiological and hypothermic conditions, and, optionally, (8) glutathione.

In a preferred embodiment, the purge solution of the blood substitute contains $H_2PO_4^-$ in a concentration of from 1.0 to 3 mM and $HCO_3^-$ in a concentration of from 20 to 30 mM and the maintenance solution of the blood substitute also contains $H_2PO_4^-$ in a higher concentration of from 5 to 15 mM and $HCO_3^-$ in a lower concentration of from 3 to 7 mM.

In another preferred embodiment the maintenance solution contains about 5 mM glucose, about 20 mM sucrose and about 20 mM mannitol. In another preferred embodiment, the impermeant anion of the maintenance solution is lactobionate at a concentration of about 100 mM.

In yet another preferred embodiment the macromolecular oncotic agent of the purge and maintenance solutions of the blood substitute is Dextran 40.

In still another preferred embodiment of the invention the substrate for regeneration of ATP in both the purge solution and maintenance solution is adenosine. In another preferred embodiment, the purge and maintenance solutions each further contain a membrane channel blocker, such as a fast channel blocker (e.g. lidocaine) and a calcium channel blocker (e.g. nicardipine). In yet another preferred embodiment each of the purge and maintenance solutions contain an iron-chelating agent (e.g. Deferoxamine). And in another preferred embodiment, the purge and maintenance solutions each contain an inhibitor of xanthine oxidase (e.g. Allopurinol) and a 5′nucleotidase inhibitor (e.g Allopurinol).

In another aspect of the invention, there is provided a method for preserving tissue e.g. skin, heart, kidneys, etc. for transplantation or grafting. According to this method the tissue or organ to be transplanted or grafted is infused with an intracellular hyperkalaemic solution containing (1) an aqueous solution of electrolytes including potassium ions at a concentration range of from 35 to 45 mM, sodium ions at a concentration range of from 80 to 120 mM, magnesium ions at a concentration range of from 2 to 10 mM, and calcium ions at a concentration range of from 0.01 to 0.1 mM, (2) a macromolecular oncotic agent, (3) a biological pH buffer effective under physiological and hypothermic conditions, (4) at least one simple sugar, (5) mannitol, (6) an impermeant anion, and (7) a substrate for the regeneration of ATP, and, optionally,
(8) glutathione.

In a particular embodiment of this aspect of the invention, that is, a method for preserving a donor tissue or organ with the aforementioned intracellular hyperkalaemic (i.e. maintenance) solution, an extracellular normokalaemic purge solution, preferably the aforementioned purge solution, is used to flush the donor tissue or organ prior to introduction of the intracellular hyperkalaemic solution.

In still another aspect of the invention, there is provided a method of performing a bloodless hypothermic procedure upon a euthermic subject in need thereof including the steps of:
(a) lowering the subject's core body temperature to a temperature above ice point and insufficient to cause cardiac fibrillation;
(b) perfusing the subject with an amount of a first perfusate sufficient to remove essentially all of the subject's circulating blood, said first perfusate containing a first aqueous solution of electrolytes at physiological concentrations, a macromolecular oncotic agent, a biological pH buffer effective at physiological and hypothermic temperatures, a simple sugar, a substrate for the regeneration of ATP and, optionally, glutathione,
(c) replacing essentially all of the circulating first perfusate with a second perfusate containing a second aqueous solution of electrolytes including potassium ions at a concentration range of from 35 to 45 mM being sufficient to arrest cardiac contractile activity abruptly, sodium ions at a concentration range of from 80 to 120 mM, magnesium ions at a concentration range of from 2 to 10 mM, and calcium ions at a concentration range of from 0.01 to 0.1 mM, a macromolecular oncotic agent, a biological pH buffer effective under physiological and hypothermic conditions, at least one simple sugar, mannitol, an impermeant anion, a substrate for the regeneration of ATP, and, optionally, glutathione;
(d) performing the hypothermic procedure on the patients;
(e) replacing essentially all of the circulating second perfusate with the first perfusate; and
(f) reintroducing blood into the subject.

In a preferred embodiment of the bloodless hypothermic procedure, erythrocytes are removed from the subject's blood during step (b) and the erythrocytes are added back to the subject's blood prior to reintroducing blood into the subject.

In another preferred embodiment of this aspect of the invention the amount and rate of introduction of any fluid into the subject is controlled by removing from the subject's circulation sufficient fluid to maintain the pulmonary arterial wedge pressure at 5 mM Hg or less and by maintaining an adequate hydrostatic pressure between the subject and the venous outflow at the circulating pump.

According to still another aspect of the invention relating to tissue/organ preservation the cell-free hypothermic blood solutions for maintenance and flush are used for whole-body perfusion of a cadaver soon after death and the whole body refrigerated, whereby multi-organ preservation prior to harvesting individual or multiple organs for transplantation is made possible.

In still yet another aspect of the invention, applicable in the fields of trauma and resuscitative medicine the novel cell-free hypothermic blood substitute is used for sustaining and reviving hemorragically shocked patients. As soon as possible after the trauma patient is received the patient is cooled down, put on by-pass, and then treated with the invention purge and maintenance solutions such as described for bloodless hypothermic surgery. This treatment will allows the physician much needed time to make a careful assessment of the injury and to effect the repair.

DETAILED DESCRIPTION OF THE INVENTION

The blood substitute of this invention is an aqueous solution without any of the cells normally found in whole blood or blood plasma and, as such, can generally be safely stored for much longer periods than whole blood or blood plasma and can be used without cross-matching or haplotyping between donor and recipient. Since the blood substitution solutions of this invention are totally synthetically produced there is substantially no risk of blood contaminants, such as bacterial, viral or other blood contaminants being introduced into the solutions. This is especially important in this age of hepatitis, AIDS and other blood transmitted diseases.

The preservation or maintenance solution according to the invention is capable of protecting living tissues, such as skin, corneas, organs, such as, for example, heart, lung, kidney, liver or pancreas, and organ parts, such as, for example, muscles, pancreatic islets, heart valves, and the like. Such protection includes protection from damage caused by ischemia and/or anoxia during storage prior to transplantation in a subject. The maintenance solution contains
(1) an aqueous solution of electrolytes including potassium ions at a concentration range of from 35 to 45 mM, sodium ions at a concentration range of from 80 to 120 mM, magnesium ions at a concentration range of from 2 to 10 mM, and calcium ions at a concentration range of from 0.01 to 0.1 mM,
(2) a macromolecular oncotic agent,
(3) a biological pH buffer effective under physiological and hypothermic conditions,
(4) at least one simple sugar,
(5) mannitol,
(6) an impermeant anion, and
(7) a substrate for the regeneration of ATP, and, optionally,
(8) glutathione.

Each of the components (1) through (7) and (8) (when present) of the maintenance solution is selected for whole body bloodless hypothermic procedures as well as for optimal preservation of organs. The blood substitute maintenance solution is described hereinbelow in further detail.

In general, the maintenance solution in addition to its role as a cell-free hypothermic blood substitute may be used for the preservation of tissues, e.g. skin, organs, such as heart, lungs, kidney, liver or pancreas for transplantation or grafting. The application of the maintenance solution to bloodless hypothermic treatment is described below.

For organ preservation, the organ (e.g. kidney) is removed from a donor (living, or promptly following death) and immediately thereafter infused with the maintenance solution. In the case of removal following death, the organ should be removed as soon as possible to prevent ischemic damage, generally within about 30 minutes to about 90 minutes. The organ is stored in excess maintenance solution at a temperature in the range of from about 2° C. to about 12° C. until later transplantation in a patient. Developments in the field of ex vivo organ preservation have advanced during the past quarter century to the point where organs for transplantation can be safely stored for variable periods depending upon the nature of the organ. Kidneys, livers and pancreases can be stored for one to several days, but the clinically accepted limits for hearts is currently only about 6 hours or less. The present maintenance solution provides protection of various organs for at least the maximum allowable storage time for each organ.

In addition to preservation of individual tissues or organs the blood substitutes of this invention may also be used for whole body preservation of cadavers, including brain-dead individuals. In this manner preservation of the individual organs and other tissues for up to 8 hours or more can be achieved. The cadaver may be treated in substantially the same manner as described herein for bloodless hypothermic surgery, except that after the introduction of the maintenance solution at hypothermic temperature the individual is maintained under hypothermic temperature until such time as one or more organs are needed and are then harvested for use. The removed organs are then stored for transportation in additional fresh maintenance solution as needed.

The purge solutions of this invention may also be used as a vehicle solution for various drugs and pharmaceutical agents that will protect or reverse reperfusion injury in a previously stored organ when flushed with the purge solution prior to transplantation, for example, see the Carolina Rinse, incorporated herein by reference, for a description of suitable drug and pharmaceutical agents. Thus, the purge solution and maintenance solution may be used for isolated organ preservation as well as for whole body preservation and whole body perfusion in profound hypothermia.

The maintenance solution of the present invention has also been found to preserve and protect tissues, e.g., skin, from storage damage and possibly from the harmful effects of toxins and chemical toxicants. Thus, the present maintenance solution is also applicable to the storage of tissues, such as skin and corneas, for example, for later transplantation on, for example, burn patients, as well as to the protection of human skin against the harmful effects of toxins and toxicants, such as may be present in polluted environments, against chemical or germ warfare, and the like. For preservation of skin and corneal tissue for later transplantation, the tissue is removed from the donor and stored in maintenance solution for at least one week and up to about 2 to 4 weeks at 4° C. until transplantation. Furthermore, it is expected that preservation of frozen skin for several months to one or more years can be achieved if cryoprotectants are incorporated in the maintenance solution.

Human Epidermal skin models (HEM) have been developed and are being used to identify cytoprotective compounds of military interest and of pharmaceutical importance. Moreover, the use of synthetic skin models, as acceptable alternatives to the use of animals for toxicity testing, is being explored e.g. in the cosmetic industry. There is also the possibility that synthetic human epidermal skin will be of great benefit in the treatment of burns patients. However, research in these areas is hampered by the difficulty of transporting HEM without significant loss of viability and some skin equivalents have only a 1–2 day shelf life after shipping.

As shown in the examples to follow the hypothermic preservation of the present invention fluid can extend the life of skin tissue. In a study using a human epidermal skin model, the maintenance solution was shown to have the potential of extending tissue life.

For in vivo protection of the skin from harmful toxins, such as noxious gases, the maintenance solution may be applied topically to the skin. The maintenance solution is replaced as needed.

The present invention is also directed to a two component (solution) cell-free hypothermic blood substitute that contains (A) a purge solution and (B) the maintenance solution described above. The purge solution is designed for flushing blood from a subject or organ donor during cooling before being replaced by the maintenance solution. It is also designed to purge the system of the hyperkalemic maintenance solution during rewarming and to help flush out accumulated toxins and metabolic by-products that might promote oxidative stress and free radical injury upon reperfusion. The maintenance solution is designed to protect the brain and other visceral organs from damage caused by ischemia and/or anoxia during prolonged surgical procedures. While some of the compounds of the present blood substitute are similar to those of known intracellular flush solutions such as UW-1 Flush, Ringer's Lactate, Carolina Rinse and Krebs Bicarbonate, and the base and maintenance solutions of U.S. Pat. No. 4,923,422, the present invention was specifically designed to minimize tissue damage during prolonged hypothermia and to decrease the post-operative recovery time. As a result of these improved characteristics, the blood substitute of the present invention is more efficacious than previously known blood substitutes in protecting organs during storage for transplant and protecting the brain and other organs of a subject during prolonged surgery. Moreover, use of the present blood substitutes results in significantly shorter recovery periods of subjects as well as allowing for the extension of time during which the patient is exposed to cardiac arrest during ultra-profound hypothermia. With the use of the present blood substitutes subjects may be exposed to ultra-profound hypothermia for up to 3 hours with good recovery times and universal preservation of all of the tissues of the body. Recovery periods range from a few hours post-operatively to a few days, with only mild to moderate temporary neurological deficit. Moreover, tissue biochemistry is quickly returned to normal ranges, for all enzymes and electrolytes examined, within hours to days of surgery using the present blood substitute. Basically, tissue biochemistry is not as adversely effected by use of the present combination of blood substitutes as with the use of previous blood substitutes or with the use of extracellular purge blood substitute alone.

The two component (solution) blood substitute of this invention may also be of significant benefit in connection with trauma and resuscitation medicine. For example, in connection with a patient suffering from hemorrhagic shock the patient may be sustained and revived using the purge and maintenance solution in the manner described above for ultra-profound hypothermia. In this manner the patient may be sustained sufficiently long to allow the physician to make an accurate assessment of the injury, e.g. tissue and organ and vascular damage, and to carry out the necessary repairs.

Both the purge and maintenance solutions of the present blood substitute are cell-free (e.g. red blood cells, white blood cells, macrophages, etc.). Both solutions contain an aqueous solution of electrolytes, at physiological (e.g. normokalemic) concentration in the purge solution and hyperkalemic in the maintenance solution; a macromolecular oncotic agent; a biological pH buffer having effective buffering capacity in the range of physiological and hypothermic pH, and at least one simple nutritive sugar. The individual components of the inventive blood substitute solutions will now be described in greater detail.

(1) Aqueous Solution of Electrolytes

The ionic component of the purge solution is based upon normal extracellular fluid values and, as such, is similar to that of Krebs-Ringer balanced salt solution. However, the present purge solution contains less glucose than Krebs-Ringer balanced salt solution in order to prevent exogenous overload during hypothermia, which can potentiate lactate production and intracellular acidosis by anaerobic glycolysis. The electrolytes at physiological concentration include ions of sodium, potassium, calcium, magnesium, chloride, sulfate, phosphate and bicarbonate in concentrations approximating that found in blood plasma.

The maintenance solution includes ions of sodium, potassium, calcium, magnesium and chloride. However, the maintenance solution has significantly reduced sodium and elevated potassium concentrations compared with normal extracellular values to restrict passive diffusional loss of cellular potassium and sodium gain. Magnesium ion is at a concentration sufficient to inhibit the loss of intracellular magnesium and to inhibit the flux of calcium ions across cell membranes.

During profound hypothermia, the membrane pumps of the cells are switched off. Consequently, ions, principally potassium and sodium, exchange passively across the cell membrane. The present maintenance solution is designed to compensate for potassium efflux and sodium influx. To this effect the maintenance solution contains about 35 to 45 mM potassium ions, more preferably about 42 mM, and about 80 to 120 mM sodium ions, preferably about 100 mM.

Chloride concentration in the maintenance solution is greatly reduced compared to physiological concentrations but some chloride is present to maintain a near physiological product of potassium and chloride concentrations. Chloride ion concentration is in the range of about 2.5 to 7.0 mM.

The purge and maintenance solutions of the blood substitute, according to the invention, also include a concentration of divalent metal ions of a type and in an amount sufficient to displace or block the effects of calcium ion at the cellular membrane. Some metals that produce divalent ions, such as cadmium and beryllium, are poisonous to mammals and may not be used for this purpose. Magnesium ion is preferred and it is furthermore preferable to supply magnesium in the purge solution by the addition of a non-chloride salt of magnesium. Magnesium sulfate is the preferred form in the purge solution, whereby increase in the concentration of magnesium ion can be obtained without effecting the chloride ion concentration of the blood substitute. Magnesium chloride is preferred for the maintenance solution. The additional magnesium ion in the maintenance solution of the blood substitute is believed to displace calcium ion in the so-called cellular membrane calcium channel. It is believed that magnesium acts as a physiological calcium channel blocker. The effect achieved with magnesium ion may also be achieved through the use of drugs, namely, the so-called calcium channel blockers, such as Nicardipine, which affect this same physiological mechanism.

The magnesium level is elevated relative to that of the purge solution to both inhibit loss of intracellular magnesium and to impede metabolism of ATP and competitively inhibit binding of calcium to red cell membranes as ATP reserves are depleted. The maintenance solution contains about 2 to 10 mM $Mg^{++}$, preferably from about 2.5 to 7.5 mM $Mg^{++}$, such as about 5 mM $Mg^{++}$.

Calcium is normally chelated by ATP but upon its release it binds to red blood cell membranes and increases their rigidity and blocks microcirculation. There is ample evidence that in the areas of cardioplegia and myocardial preservation the use of high magnesium ($Mg^{++}$) and very low, but not zero, calcium results in improved survival of organs. Preferably, the calcium ion concentration is from about 0.01 to 0.1 mM, preferably 0.01 to 0.07 mM.

As noted above, Nicardipine or other calcium channel blockers, such as Verapamil, Nifedipine, Diltiazem and Lidoflazine, for example, may be included in the purge and maintenance solutions as a calcium channel blocker to minimize calcium overload. Normally, the concentration of cytosolic calcium is much lower than in extracellular fluid ($10^{-7}$M and $10^{-3}$M, respectively). This gradient is finely regulated with calcium entering the cell exclusively through specific voltage or receptor-operated channels; it is extruded from the cytosol by a sodium/calcium exchange mechanism and by active transport. Raised cytosolic calcium levels are associated with numerous biochemical changes as well as altered cell morphology including blebbing. One important result of raised cytosolic calcium is the activation of membrane bound phospholipases that remove fatty acids, particularly arachidonic acid, from the cell membranes. The resulting increase in residual membrane lysophosphatide residues alters the bilayer configuration that may in turn predispose to further free radical damage. Such effects can be prevented by inclusion of Nicardipine or other calcium channel blockers. Preferably, Nicardipine or other calcium channel blocker is included in the purge and maintenance solutions at a concentration of from 1 mM to 3 mM, most preferably about 2 mM.

The ionic balance of the maintenance solution is carefully selected to restrict passive exchange of ions across cell membranes during hypothermia and at the same time maintain ionic strength. The balance of the monovalent and divalent cations, in particular, is chosen to provide better control of ionic imbalances for tissues than that obtained using other available media that have been designed for the preservation of specific organs. For example, the concentration of potassium ion ($K^+$) is elevated to restrict loss of intracellular potassium but the concentration is much lower than found in most organ preservation solutions (e.g. Collins, Eurocollins, Sacks, UW and hypertonic citrate) since very high potassium levels may be detrimental and injurious to cardiac tissue, resulting in contraction band necrosis, for example. Moreover, for applications of the maintenance solution as a blood substitute during surgery it is also imperative that the level of $K^+$ can be readily reduced to physiological levels ($<6$ mM) during rewarming in order that the arrested heart can be reactivated.

The present maintenance solution has an elevated $Mg^{2+}$ concentration to prevent loss of intracellular $Mg$ and also impede metabolism of ATP and competitively inhibit binding of calcium to red blood cell membranes as ATP reserves run down. As noted previously, in the area of cardioplegia and myocardial preservation there is good evidence for improved survival using high $Mg^{2+}$ and very low, but not zero, calcium. To avoid the putative calcium paradox, calcium is included in the maintenance solution at a very low concentration, i.e. in the range of about 0.01 to 0.1 mM, preferably 0.01 to 0.07 mM, such as about 0.05 mM.

It is preferred that the desired concentrations of electrolytes of both the purge and maintenance solutions are obtained by dissolving salts of the desired ions in water, preferably distilled water.

(2) Macromolecular Oncotic Agent

The macromolecular oncotic agent of the blood substitute is required to maintain oncotic pressure equivalent to that of blood plasma. Any oncotic agent that is of a size that does not readily escape the circulation by traversing the fenestrations of the capillary bed may be used. Such oncotic agents include, for example, blood plasma expanders which are generally known as macromolecules having a size sufficiently large to prevent their escape through the circulatory capillary bed into the interstitial spaces of the body. Human serum albumin is one well known blood plasma protein that is used as a blood plasma expander. Polysaccharide blood plasma expanders are generally characterized as glycan polymers.

Hetastarch (a product of American Home Products) is an artificial colloid derived from a waxy starch composed almost entirely of amylopectin with hydroxyethyl ether groups introduced into the alpha (1–4) linked glucose units. The colloid properties of a 6% (wt/wt) solution of hetastarch approximates that of human serum albumin.

Other polysaccharide derivatives may be suitable as oncotic agents in the blood substitute according to the invention. Among such other polysaccharide derivative are hydroxymethyl alpha (1–4) or (1–6) polymers. In general, it is preferred that the polysaccharide is one that is non-antigenic. Cyclodextrins may be suitable as oncotic agents in the blood substitute according to the invention.

Preferred oncotic agents are polymers of D-glucose, and in particular D-glucose linked predominantly in alpha (1–6) linkage, known as dextran. In the blood substitute according to the invention, it is necessary that the polysaccharide be sufficiently large so as not to escape readily from the capillary bed of the patient's or donor's vasculature. High molecular weight polysaccharides such as Dextran 70 having a molecular weight of about 70,000 daltons are generally less preferred because they increase viscosity of the colloidal solution and impair the achievement of high flow rates. More preferred to achieve high flow rates are polysaccharides in a molecular weight range of 30,000 to 50,000. Most preferred is Dextran 40 having a molecular weight of about 40,000. Dextran has been shown to be effective in improving the efficiency of removal of erythrocytes, partly by inhibiting red cell clumping, but also by increasing the intravascular osmotic pressure, thereby drawing additional fluid into the capillaries, diluting the contents and improving fluidity while dilating the capillaries and reducing vascular resistance. Dextran is preferred to HES, another colloid that may be used in the present invention, because the solution will have a lower viscosity, and any colloid that does permeate the vascular bed will be more readily removed which is important for a whole body perfusion. Dextran is widely used clinically as a component of plasma expanders and is readily and rapidly excreted by the kidneys.

Under some circumstances, particularly in treatment of cerebral ischemia, it may be desirable to use blood substitute solutions containing higher molecular weight colloids despite their higher viscosity and relatively low flow rates. Such solutions, which may be more effective in preventing tissue swelling due to their lower rates of leakage from capillaries, may be particularly useful in the treatment of cerebral ischemia at hyperbaric oxygen tensions and for the management of edema to remove accumulated interstitial fluid. In such circumstances, it may be desirable to use higher molecular weight polysaccharide, such as dextran, in a molecular weight range of 50,000 to 70,000.

At reduced temperatures the negatively charged proteins and other metabolites within cells give rise to a colloid osmotic pressure which is no longer counterbalanced by active membrane pumps. The result is that cells swell by imbibing water and eventually lyse. The solutions of the present invention maintain the proper hydraulic balance in the cells during hypothermia. The concentration of the polysaccharide in the purge and maintenance solutions of the present blood substitute is sufficient to achieve, when taken together with electrolytes and simple sugar discussed below, a colloid osmotic pressure approximating that of normal human serum, namely, about 28 mm Hg. In particular when Dextran 40 is used at a concentration of about 6% Dextran 40 (wt/wt) or when about 60 grams (g) Dextran 40 per liter (l) of water is used osmolality of the blood substitute according to the invention will be in a range of about 300 to 370 milliosmoles (mosm), with an osmolality of about 305–315 mosm for the purge solution and 350 to 370 mosm for the maintenance solution being preferred.

(3) Biological pH Buffer

The pH of the purge and maintenance solutions of the blood substitute is generally maintained at about 7.8 at 10° C. The pH is maintained by the use of a biological buffer such as Hepes buffer, for example. Such buffers have buffering capacities in the range of physiological pH between about 7.2 and 7.9 at 37° C., but may have a wider range. Acidosis is a particular problem during hypothermia and has heretofore received relatively little attention. To combat acidosis, in a preferred embodiment, the present blood substitute solutions contain, in addition to the synthetic biological buffer, $HCO_3^{31}$ and $H_2PO_4^-$. Preferably, the concentration of $HCO_3^-$ in the purge solution is in the range of about 20 to 30 mM, preferably about 25 mM and the concentration of $H_2PO_4^-$ is in the range of from about 1 to 2 mM. In the maintenance solution, $HCO_3$ is present at a concentration of from about 3 to 7 mM, preferably about 5 mM and $H_2PO_4^-$ is present at a concentration range of from about 5 to 15 mM, preferably about 10 mM. Preferably, the biological pH buffer is a large sulfonic acid buffer that will not penetrate into cells and will help prevent osmotic swelling. Preferably, the sulphonic acid buffer is N-2-hydroxyethylpiperazine-N'-2-hydroxypropanesulfonic acid (HEPES) buffer which has a useful pH range between 6.8 and 8.2 at normal temperatures. Other zwitteronic sulfonic acid buffers such as 3-(N-morpholino) propanesulfonic acid (MOPS), pH range 6.5–7.9, N-tris(hydroxymethyl)methyl-2-aminoethanesulfonic acid; 2-((2-hydroxy-1,1-bis(hydroxymethyl)ethyl)amino) ethanesulfonic acid (TES), pH range 6.8–8.2, 3-(N-tris(hydroxy-methyl) methylamino)-2-hydroxypropanesulfonic acid (TAPSO), pH range 7.2–8.2,4-(2-hydroxyethyl)-1piperazinepropanesulfonic acid (EPPS), pH range 7.3–8.7, and tris(hydroxymethyl)aminomethane (THAM) may be used.

Synthetic zwitterionic sulfonic acid buffers are further preferred because they possess superior buffering capacity at reduced temperatures compared with natural biological buffers such as phosphate and bicarbonate. Moreover, the temperature coefficient of the sulphonic acid buffers is equal to or greater than that of the ion product of water (pKw) thereby providing effective control of pH under hypothermic conditions by maintenance of a constant degree of alkalinity in relation to the neutral point of water in accordance with alphastat regulation.

(4) Simple Sugar

Both the purge solution and maintenance solution of the blood substitute according to the invention include a simple nitritive sugar. Simple nitritive sugars include sucrose, fructose and glucose or dextrose, which is alpha D-glucose. Most preferred is glucose. In general, in the blood substitute according to the invention, the concentration of the simple sugar will be in a range of from about 1 mM to about 10 mM. Glucose at a concentration of about 0.9 g (5 mM) per liter glucose is preferred in both the purge solution and maintenance solution.

Depending upon the specific purpose for which the blood substitute is to be used the concentration of the nutritive sugar in the purge and maintenance solutions may be further varied in a range between about one millimolar (1 mM) and one molar (1M). Thus, if the blood substitute is to be used to maintain a subject during a surgical procedure the lower concentration of glucose of about 1 to 10 mM is used, preferably about 5 mM in both the purge and maintenance solutions. However, if the blood substitute is used in the therapy of shock, such as surgical shock, the molarity of glucose is increased above 20 mM and preferably the concentration of glucose is increased to a range between about 100 mM and 1M. The use of solutions containing higher concentrations of simple sugar, used for the treatment of surgical shock may be immediately followed by administration of purge or maintenance solution containing a low concentration of simple sugar to wash out the high sugar concentration.

(5) Mannitol

Mannitol in the maintenance solution serves dual purposes as both an impermeant and as an efficient hydroxyl radical scavenger. It has previously been demonstrated that the use of mannitol in non-blood product based blood substitutes, when administered to living subjects is associated with significant decreases in pH that are usually uncontrollable even with dialysis (e.g., Segall, et al., U.S. Pat. No. 4,923,442). However, in the present blood substitute, proper pH is maintained despite the presence of 10 to 20 mM mannitol, preferably about 20 mM mannitol.

(6) Impermeant Anion

The maintenance solution of the present blood substitute is a hyperosmolar solution containing an osmoticum including sucrose, a large impermeant anion and mannitol in addition to another simple sugar, as well as sucrose. The large impermeant anion of the osmoticum is a principal component of the maintenance solution and is used to counteract cell swelling during cold exposure. A number of appropriate molecules can be used, however, preferably, lactobionate is selected because it is biocompatible, and it is also a strong chelator of calcium and iron and may, therefore, contribute to minimizing cell injury due to calcium inflow and free radical formation. The concentration of the large impermeant anion is preferably in the range of 80 to 120 mM, most preferably about 100 mM. Other impermeant anions which may be used in place of, or together with, lactobionate include for example, gluconate, citrate, glycerophosphate etc. In addition, various sulphonate buffers, such as HEPES may also provide an impermeant function, insofar as its molecular size is sufficient to remain outside the cellular membrane.

(7) ATP Substrate

Also included in the purge and maintenance solutions of the blood substitute is an essential substrate for the regeneration of ATP during rewarming. Adenosine is the preferred ATP substrate and also serves as a vasoactive component to facilitate efficient vascular flushing by vasodilation. The amount of adenosine is generally higher in the maintenance solution than in the purge solution and is in the range of from about 0.5 to 2 mM, preferably about 1.0 mM in the purge solution and in the range of from about 1.5 to 3 and preferably about 2.0 mM in the maintenance solution. Other known substrates for the regeneration of ATP such as fructose, ribose and adenine may also be used in place of a portion or all of the amount of adenosine.

(8) Glutathione

Glutathione is an optional but preferred additive in the purge and maintenance solutions. Glutathione functions as a cellular antioxidant and hydroxyl radical scavenger as well as a cofactor for the enzyme glutathione peroxidase, which enables metabolism of lipid peroxides and hydrogen peroxide. Glutathione, when present, may be included in either or both solutions at a concentration in the range of from about 1 to about 5 mM, and preferably about 3 mM in both solutions.

(9) Other Optional Additives

An inhibitor of xanthine oxidase, such as, Allopurinol, may also be included in the purge and maintenance solutions of the present invention. Xanthine oxidase is formed by calcium activated proteolysis and generates superoxide free radicals. Allopurinol may, therefore, be effective in preventing reperfusion injury. Also, in kidneys damaged by warm ischaemia, allopurinol significantly reduces erythrocyte "trapping" in the medullary region. Oxygen free radicals are thought to play a role in the increase of leukocyte adhesiveness to capillary endothelial membranes. Allopurinol is also a 5'-nucleotidase inhibitor. As ATP (adenosine triphosphate) and ADP (adenosine diphosphate) reserves are depleted in ischemic tissue, the accumulating AMP (adenosine monophosphate) is dephosphorylated by 5′-nucleotidase to adenosine which is freely diffusible. Such nucleotides are lost from cells and are no longer available for resynthesis of ATP, even if chemical energy is made available. The presence of allopurinol in the purge and maintenance solutions is believed to help prevent the dephosphorylation of AMP and thus, helps maintain the availability of ATP. The concentration of allopurinol in the present solutions is in the range of from about 0.05 to about 2.5 mM, preferably about 1.0 mM in both solutions.

Deferoxamine or other iron-chelating agent may also be included in the purge and maintenance solutions. Deferoxamine is a potent iron-chelating agent that is used clinically for treating thalassemia and iron overload patients. It may be included in the present blood substitute as an agent against lipid peroxidation which inhibits iron catalyzed formation of hydroxide via the Haber Weiss reaction. Preferably, when deferoxamine is included, it may be present in both solutions at a concentration of from about 0.05 to about 2 mM, preferably about 1.0 mM.

The blood substitute based on the maintenance solution as described above, alone or together with the purge solution as described above, may be used in a variety of specific procedures as will be further explained hereinbelow. Moreover, a blood substitute containing the present maintenance solution and a purge solution other than the present purge solution can also be used in a variety of procedures. For example, the present maintenance solution can be used in combination with various purge solutions such as Kreb's bicarbonate, Ringer's lactate, or Carolina Rinse. In each of these procedures the purge solution is administered after partial exsanguination of the subject patient or donor or is administered while progressively exsanguinating the patient or donor and to gradually lower the body temperature of the subject until a low temperature is reached. Once the subject's body temperature is lowered sufficiently that cardiac fibrillation cannot occur, the purge solution is removed and replaced with the maintenance solution and the subject is maintained with this solution until revival of the subject is desired. Following the particular procedure to which the patient is subjected, the maintenance solution is replaced with the purge solution followed by replacement of the purge solution with blood (which may, preferably, be the patient's own blood previously collected) and the subject is rewarmed and revived as described below.

In general, the use of the blood substitute during whole body hypothermia and bloodless surgery is described as follows. The subject is anesthetized and prepared for surgery. The subject is connected to a clinical cardio-pulmonary bypass circuit modified by the addition of a drain line connected to the venous side of the circuit to facilitate exsanguination and a port connecting the oxygenator to a reservoir to permit the blood substitutes to be added to the circuit. The subject's body is cooled by placing on a bed of ice, immersion in an ice bath or wrapped in a jacketed cooling blanket, and the body temperature is gradually lowered. Prior to the introduction of the purge solution, but after the body temperature of the subject has been lowered to a point before cardiac fibrillation occurs, a substantial volume of the subject's blood is removed using sterile technique and placed preferably in sterile cold storage. Preferably, a significant portion of the subject's blood will have been removed prior to introduction of purge solution. This removal of the subject's blood is useful in controlling the pulmonary arterial wedge pressure and thereby minimizes damage to the subject's lungs. This whole blood can be reintroduced during the revival, rewarming and recovery period in lieu of heterologous transfusion.

Biochemical changes during cooling and anoxia cause changes to the membranes of the subject's red cells such that they become less pliable and deformable leading to clumping and blockage of capillaries. The patency of the microvasculature can be severely compromised by this mechanism leading to the "no-reflow phenomenon" upon reperfusion. In a preferred embodiment, these events and the risk of microinfarct formation are minimized by efficient removal of erythrocytes during the hypothermic perfusion. The subject's erythrocytes are later added back to the removed blood prior to reintroducing the blood into the subject. In fact, it is one of the features of the present invention that all of the patient's blood is purged and replaced by the maintenance solution, making the hypothermia treatment wholly bloodless and, ultimately, safer for the patient.

The extracorporeal pump and oxygenator is primed with purge solution pre-chilled to an appropriate temperature in the range 0° to 20° C. depending upon the desired cooling rate, purged of bubbles, and at least one volume (each volume approximately equal to the circulatory volume of the subject) of the cold solution is circulated through the subject while monitoring pulmonary arterial perfusion or wedge pressure (PAW) in the desired range. The pump is positioned such that it is significantly lower than the subject. Positioning the subject at an adequate distance above the pump provides an adequate hydrostatic head to enable superior control of the pulmonary arterial wedge pressure and effective drainage to control fluid exchange and avoid fluid retention and overload as compared to placement of the subject at a level only marginally above or level with the pump.

As purge solution is introduced fluid volumes and PAW are maintained by collecting excess volumes of fluid. The drained blood may be retained for subsequent autotransfusion and collected effluent of diluted blood may be retained and the blood cells collected therefrom by known means such as centrifugation. The blood cells so collected may be reintroduced into the subject during the revival, rewarming and recovery period as well. The subject's core temperature is monitored and at a substantially hypothermic temperature, but one above that at which cardiac fibrillation caused by hypothermia usually occurs in subjects of the size and type undergoing the procedure, at least one system volume of the maintenance solution is introduced into the subject to rapidly cause cardiac arrest by virtue of the cardioplegic properties of the maintenance solution. (Whenever one begins to introduce one of the solutions of the blood substitute into the subject, care is taken not to dilute the solution being introduced with solution remaining in the fluid reservoir of the pump circuit. Excess solution in the reservoir is removed from the reservoir or circulated through the subject before a subsequent solution is introduced).

One system volume, which is defined as the volume equal to the combined volume of the subject's blood and the volume in the extracorporeal circuit, of maintenance solution should be replaced with another system volume about two times at regular intervals during the time of maintenance of the subject at the lowered temperature. Circulation, oxygenation and core cooling using an extracorporeal membrane, hollow fiber or bubble oxygenator with a heat exchanger should continue when possible with a Swan-Ganz catheter inserted in the pulmonary artery to measure the PAW or some other means to continuously monitor and, optionally, control left ventricular end diastolic pressure. This pressure should be kept below 10 mm Hg during the entire procedure. It is preferred that PAW be kept below 5 mm Hg during the procedure. The respiratory system should be kept at about 3 to 5 mm Hg of positive end expiratory pressure (PEEP). Alternatively, pulmonary airway pressure (PA), measured as inspiratory pressure, is monitored and kept below about 12 mm Hg.

In general, at least three system volumes of this solution are circulated. During the period when the maintenance solution is circulated, the hematocrit of the subject is monitored. It is preferred to introduce additional maintenance solution and to remove at least an equivalent amount of maintenance solution from the subject whenever the subject's hematocrit reaches a value of 2% or greater, thereby maintaining the subject's hematocrit below 2%. In this manner blood cells sequestered in the subject's body may be progressively removed and a hematocrit approaching zero can be maintained during the procedure. In this manner the blood substitute according to the invention is used to essentially completely flush blood from the subject's circulation. This progressive removal of sequestered blood cells during the period when the subject is being maintained under hypothermic conditions, which is accomplished by monitoring the hematocrit, may be important in obtaining successful recovery of the subject during and after the warm up and post procedure phase. It is believed that even small amounts of blood circulated at low temperature can cause significant problems, such as pulmonary leucocytosis, on recovery.

The pH of the maintenance solution circulating in the subject is also monitored to remain in a range of from about 7.3 to 7.7, as measured at 37° C., with no correction for the actual temperature of the solution when it is in the subject. It is preferred to introduce additional maintenance solution and to remove an equivalent amount of maintenance solution from the subject whenever the pH falls or rises outside this range thereby maintaining the subject's pH within the 7.3 to 7.7 range at 37° C.

Recovery of the subject starts with replacing the maintenance solution with the purge solution. A volume of the purge solution sufficient to completely wash out the maintenance solution is used. In general, at least 3 volumes, each approximately equivalent to the subject's blood volume, are used. After sufficient purge solution has been circulated to wash out the maintenance solution, rewarming of the subject is initiated. It is preferred to maintain a 7° to 10° C. difference between the core temperature of the subject and the purge solution added to the system during recovery. When the subject's core temperature reaches approximately 9° to 10° C., whole blood (initially at about 10° C.) is added until the hematocrit reaches approximately 20 and temperature is in the range of 10° to 20° C. or the temperature at which cardiac activity starts. If fibrillation occurs it may be necessary to defibrillate by electro-stimulation or other known means. Also, if necessary, anti-arrythmia drugs such as lidocaine and cardiac-stimulants such as dopamine and epinephrine can be administered. Ventilation of the subject is restarted soon after regular cardiac activity has been reestablished if the subject does not re-establish breathing spontaneously. Surface warming may be started at this point and blood is added until the hematocrit reaches 20 to 40. During the rewarming phase pH may drop significantly, and physiological pH of 7.3 to 7.4 is reestablished by slow addition of a solution of $NaHCO_3$ alone or in conjunction with placing the subject on dialysis until pH stabilizes.

More blood or the subject's own packed cells concentrated from effluent previously removed is added back to the subject's circulation. Surgical wounds are closed and the patient is allowed to revive and is treated in intensive care as necessary.

The solutions which make up the blood substitute of the present invention are preferably administered to the subject when the subject's body temperature has already been lowered to a point substantially below normal but prior to the induction of cardiac fibrillation due to hypothermia. In larger mammals in the range of 70 to 130 kilograms this temperature may be in a range of about 27° to 30° C. and in smaller mammals in the range of 10 to 30 kilograms this temperature may be in a range of about 20° to 25° C.

The following examples are intended to be merely illustrative and are not considered to be limiting of the invention claimed hereinbelow.

REFERENTIAL EXAMPLE 1

Surgical procedure and cardiopulmonary bypass

Adult mongrel dogs ranging in weight from 10 to 18 kg were used in accordance with the guidelines and standards of the United States Public Health Services for use and care of laboratory animals, and the procedure was approved by the Institutional Animal Care and Use Committee of Allegheny-Singer Research Institute.

Using an aseptic technique throughout, animals were surgically prepared for anesthesia and extracorporeal cardiac bypass. In brief, dogs were pre-anesthetized with atropine (0.04 mg/kg IM) and pentothal (10 mg/kg IV) prior to the insertion of an endotracheal tube to maintain anesthesia using an azeotropic mixture of halothane and ether (flether). Standard ECG electrodes were placed for continuous recording of heart activity, and an intravenous catheter was inserted into the cephalic vein for infusion of a plasmolyte drip (60 ml/hr). Brain, esophageal and subcutaneous temperatures were monitored continuously by appropriate placement of temperature probes. Intracranial pressure was recorded by means of an intraparenchymal transducer probe (Camino), placed in the right frontal lobe. The femoral artery and external jugular vein were cannulated to establish extracorporeal bypass circulation. The right femoral artery was cannulated to monitor systemic arterial blood pressure and for arterial blood sampling. A 7 French Swan-Ganz catheter was advanced to the pulmonary artery via the right femoral vein to monitor the pulmonary artery wedge pressure. The right femoral vein was cannulated to monitor central venous pressure. The animal's blood was anticoagulated with heparin (100 units/kg) to achieve an activated clotting time (ACT) greater than 300 seconds.

The circuit used for bypass included a centrifugal force pump (Medtronic, Biomedicus) and a membrane oxygenator. The oxygenator, which had a heat exchanger also served as a venous reservoir. This circuit closely resembled a clinical by-pass arrangement except the following modifications were installed: a drain line was connected to the venous side of the circuit to facilitate exsanguination and a port connecting the oxygenator to a funnel was introduced to permit the blood substitutes to be added to the circuit.

Preparation of Solutions

Aqueous blood substitute solutions are prepared by dissolving all chemicals and ingredients of the highest purity available in ultra pure deionized/distilled water. Where possible tissue culture tested chemicals (Sigma) are used to maximize biocompatibility. All solutions should be filter-sterilized (e.g. 0.22 μm, Gelman filters), dispensed into 1L sterile plastic bottles and stored in a cold room (4° C.) prior to use.

REFERENTIAL EXAMPLE 2

Cooling and Controlled Exsanguination

Once the bypass circuit was complete, the plasmolyte drip was stopped and surface cooling was initiated. Once esophageal (core) temperature fell to about 25° C., or the heart rate slowed to 45 beats/min., exsanguination was started. Drained blood was collected in sterile containers and kept at 4° C. Extracorporeal circulation was initiated with the purge solution to wash out the remaining blood and the entire blood volume was exchanged with the maintenance solution. Throughout this and subsequent exchanges, the operating table was raised to maintain a hydrostatic head of 40 inches above the venous return, since preliminary experiments had shown this to provide for effective drainage and control of fluid exchange necessary to avoid fluid retention and overload in the body. The purge solution was immediately exchanged with precooled (<10° C.), oxygenated ($P_{O_2}$ 500 mm Hg) maintenance solution which was also an effective cardioplegia solution. Immediately following cardiac arrest the respirator was turned off, and the maintenance solution was continuously circulated for three hours at rates of 40 to 85 ml/kg/min. yielding a mean arterial fluid pressure of 25 to 40 mm Hg.

When the temperature had fallen to below 10° C. (nadir=6.6±° C.), the hematocrit was measured to be <1% showing that complete blood substitution was achieved. During this phase the maintenance solution was completely exchanged twice at regular intervals with fresh pre-cooled maintenance solution.

REFERENTIAL EXAMPLE 3

Rewarming and Blood Replacement

After three hours of perfusion at an esophageal temperature of <10° C. the rewarming regimen was initiated using both internal and external warming. First, the maintenance solution was replaced with purge solution to purge the system of the hyperkalemic maintenance solution. The objective here was to reduce the potassium concentration to approximately 10 mM or less necessary to permit cardiac reactivation. When the esophageal temperature reached 10° C. the animal's own blood was introduced into the circuit and removal of the purge solution continued until the whole blood volume was reintroduced.

During rewarming the heart usually started and resumed normal sinus rhythm spontaneously between 11° and 20° C., otherwise electroversion (100-200 joules) was implemented. Respiration was resumed at between 24° and 34° C. The early phase of rewarming (10° to 28° C.) was controlled via the pump at a rate of 0.7±0.1° C.

min. From 28° C. dogs were allowed to warm slowly (0.09° C./min.) to normal temperature with the aid of external warming provided by a heating blanket and heat lamps. As rewarming progressed, anesthetic was given to smooth the transition from cold narcosis to recovery. The animals were then weaned from the pump, decannulated and observed during unrestricted postoperative-recovery for neurological function. Neurological evaluation was performed using Neurological Deficit Scores (NDS) based upon a modification of the well known Glasgow Scale: NDS:0=normal; 1=minimal abnormality; 2=weakness; 3=paralysis; 4=coma and 5=death.

In addition, blood and urine samples were collected at regular intervals during the days and weeks post-operatively for evaluation of biochemical status and to determine organ function.

REFERENTIAL EXAMPLE 4

Physiological and Neurological Recovery

During rewarming animals were observed closely for signs of physiological and neurological recovery. Dogs in Group 1 (discussed hereinbelow) were all successfully revived with the first heartbeat recorded in the temperature range 11° to 27° C. and regular heartbeat and sinus rhythm resuming at 26±1° C. and respiration at 21° to 32° C. Some dogs in this group required minimal intervention with electroversion and small doses of lidocaine to correct cardiac arrhythmia. By contrast, with one dog in Group II when the temperature reached between 27° and 32° C. the heart initiated a few beats before lapsing into a persistent ventricular fibrillation that was refractory to interventional correction. Electromechanical uncoupling was observed and the animal died. The remaining two animals in this group (Group II) demonstrated similar problems during the rewarming phase. However, resuscitative measures were revised in an aggressive attempt to stabilize the persistent ventricular fibrillation. These involved the administration of 15-30 meq of KCl over 10-15 min. in combination with 500 mg $Ca^{++}$ and repeated counter-shocks (100-200 joules) to return the heart to sinus rhythm. Subsequent doses of $K^+$ and electroversion were required to correct frequent relapses into ventricular fibrillation. These abnormal and aggressive resuscitative measures were eventually successful in stabilizing the hearts of these two dogs during the rewarming phase.

EXAMPLE 1

Maintenance and purge solutions according to this invention were prepared in one liter quantities as described below. The compositions of these hypothermic solutions (HTS) for the maintenance (M) and purge (P) solutions are shown in Table 1.

| Hypothermicsolution-purge (HTS-P) was prepared by dissolving the following ingredients in 1 liter of high purity water: | |
|---|---|
| Dextran-40 (Clinical Grade) | 60.000 g |
| NaCl | 6.136 g |
| KCl | 0.448 g |
| $CaCl_2.2H_2O$ | 0.221 g |
| $MgSO_4$ | 0.120 g |
| $NaHCO_3$ | 2.100 g |
| $NaH_2PO_4$ | 0.144 g |
| HEPES | 5.958 g |
| D-Glucose | 0.901 g |
| Adenosine | 0.267 g |

| -continued | |
|---|---|
| Glutathione | 0.922 g |

Hypothermicsolution-maintenance (HTS-M) was prepared by dissolving the following ingredients in 1 liter of high purity water:

| Dextran-40 (Clinical Grade) | 60.000 g |
|---|---|
| KCl | 0.559 g |
| $CaCl_2.2H_2O$ | 0.007 g |
| $MgCl_2.6H_2O$ | 1.017 g |
| $KHCO_3$ | 0.500 g |
| $KH_2PO_4$ | 1.361 g |
| Lactobionic Acid | 35.830 g |
| HEPES | 5.958 g |
| D-Glucose | 0.901 g |
| Sucrose | 6.846 g |
| Mannitol | 3.644 g |
| Adenosine | 0.534 g |
| Glutathione | 0.922 g |
| NaOH (10 Normal Standard Sol.) | 10.000 ml |
| KOH ( 1 Normal Standard Sol.) | 20.000 ml |

The pH (25° C.) was adjusted to 7.6 by titrating with concentrated sodium hydroxide solution (10 Normal NAOH).

EXAMPLE 2

This example demonstrates the production of larger quantities (18L) of HTS-M and HTS-P having the compositions shown in Table 1.

The preparation of 18 liters of purge solution (HTS-P) was carried out as follows using high purity deionized, distilled water:

A. Using a 20 liter pyrex glass bottle, dissolve 1080 g of clinical grade dextran-40 in 8000 mls of water with constant stirring.

B. In a separate flask containing approx. 6000 mls of water dissolve 4.8 g Adenosine and 16.6 g Glutathione. When these pharmacological agents have dissolved the following components are added to the same flask with constant stirring: 110.5 g NaCl, 4.0 g KCl, 37.8 g $NaHCO_3$, 2.59 g $NaH_2PO_4$, 107.2 g HEPES and 16.2 g glucose. Using volumetric flasks (2 liter) to ensure accurate volume measurements, the contents of B. are added to A. and flask B. is rinsed into A. with a further 2 liters of water.

C. Add calcium and magnesium salts at this stage by pre-dissolving 3.97 g $CaCl_2.2H_2O$ and 2.17 g $MgSO_4$ in 100 mls of water before adding to the bulk solution in A.

D. After adequate mixing (e.g. stir for at least 1 hr.) adjust the pH to 7.60 measured electrometrically at 25° C. by adding approx. 18.0 mls 10 Normal Standard NaOH.

E. Add the required balance of water to make to final volume.

The preparation of 18 liters of maintenance solution (HTS-M) was carried out as follows using high purity deionized, distilled water:

A. Using a 20 liter pyrex glass bottle, dissolve 1080 g of clinical grade dextran-40 in 8000 mls of water with constant stirring.

B. In a separate flask (4 liter) pre-dissolve 9.6 g Adenosine and 16.6 g Glutathione in approx. 3000 mls of water. When dissolved add the following components with constant stirring: 10.06 g KCl, 9.0 g $KHCO_3$, 24.5 g $KH_2PO_4$, 16.2 g glucose, 123.2 g sucrose, and 65.6 g mannitol.

C. In a separate flask (4 liter) pre-dissolve the following components in approx. 3000 mls water with constant stirring: 645 g lactobionic acid, 180 mls of 10 Normal Standardized NaOH and 107 g HEPES.

D. Using volumetric flasks (2 liter) for precise volume measurements, transfer the contents of flasks B (4 liters) and C (4 liters) into the bulk solution in bottle A.

E. Add calcium and magnesium salts at this stage by pre-dissolving 0.13 g $CaCl_2.2H_2O$ and 18.3 g $MgCl_2.6H_2O$ each in water before adding directly to the bulk solution in A.

F. After adequate mixing (stir for a minimum of 1 hr) adjust the pH to 7.60 measured electrometrically at 25° C. by adding 360 mls of 1 Normal Standard KOH and then making the final pH adjustment by adding required amounts of 10 Normal Standard NaOH.

G. Add the required balance of water to make up to final volume.

Finally, both solutions are filter-sterilized by pumping through sterile 0.22 μm filters and dispensed into 1 liter sterile bottles for refrigerated storage.

TABLE 1

Compositions of Hypothermic Solution Blood Substitutes

| Component | HTS-P millimoles/liter (mM) | HTS-M millimoles/liter (mM) |
|---|---|---|
| IONIC | | |
| $Na^+$ | 141.2 | 100.00 |
| $K^+$ | 3.0 | 42.50 |
| $Ca^{2+}$ | 1.5 | 0.05 |
| $Mg^{2+}$ | 1.0 | 5.00 |
| $Cl^-$ | 111.0 | 17.10 |
| $SO_4^{-2}$ | 1.0 | — |
| pH BUFFERS | | |
| $H_2PO_4^-$ | 1.2 | 10.0 |
| $HCO_3^-$ | 25.0 | 5.0 |
| HEPES | 25.0 | 25.0 |
| IMPERMEANTS | | |
| Lactobionate | — | 100.0 |
| Sucrose | — | 20.0 |
| Mannitol | — | 20.0 |
| Glucose | 5.0 | 5.0 |
| COLLOIDS | | |
| Dextran-40 | 6.0% | 6.0% |
| METABOLITES | | |
| Adenosine | 1.0 | 2.0 |
| Glutathione | 3.0 | 3.0 |
| Osmolality (mOsm/kg) | 305 | 350 |
| pH (25° C.) | 7.6 | 7.6 |
| $[K^+] [Cl^-]$ | 684 | 727 |

EXAMPLE 3

A first group (Group I) of test animals comprised 11 dogs that were blood substituted with a combination of the purge and maintenance solutions as described above. A second group (Group II) of three dogs was treated identically, except that these dogs were perfused throughout the hypothermic period with purge solution alone and not substituted with the maintenance solution. This group served as controls for evaluation of the merits of perfusion with the maintenance solution per se.

The first dog in Group I was maintained at 7° C. for 120 min. (cardiac arrest=149 min); but for the remaining ten animals the esophageal temperature was below 10° C. for 182±1 min. during which time a nadir core temperature of 6.4±0.1° C. and a brain nadir of 7.5±0.5° C. was recorded. The cardiac arrest time for these animals was 215±3 minutes. The core (esophageal) temperature of the control group of animals (Group II) was maintained below 10° C. (nadir=6.4±0.1) for 175±6 min. and the hearts were arrested for 193±1 min. during the procedure.

Eight dogs in Group I quickly regained full consciousness within 315±45 minutes of termination of cardiopulmonary bypass and have survived long-term (current range of 14–90 weeks) with no apparent neurological deficits. Of the remaining three in this group, two survived the procedure and regained consciousness but did not survive long-term; one died on the second postoperative day from uncertain causes but pancreatitis or hypokalemic shock were suspected; a second dog was sacrificed after four days due to the occurrence of seizures which autopsy revealed were possibly induced by the placement of the intracerebral monitoring probes; the third animal regained neurological reflexes but did not regain consciousness and died on the second day. It was observed in this animal that the ICP was high throughout and autopsy revealed bleeding tendencies in the subarachnoid space, brain stem and spinal cord as well as in other tissues. Over heparinization was suspected as a contributory factor in this single case.

In Group II, the two animals that were successfully revived using the aggressive resuscitative measures described above, have survived long-term (18 and 26 weeks before elective sacrifice) but their physiological and neurological recovery was noticeably slower. All survivors from Group I were generally active with complete recovery of motor function within 24 hours as defined by their ability to stand, walk, eat and drink. Three dogs showed extremely rapid recovery and were able to stand and walk within 12 hours of the procedure (the fastest was 5.5 hours and the mean for the group was 20±4 hours). Moreover, these animals were all able to walk normally within two days and did not show any signs of a hind-limb weakness, a problem frequently noticed and reported by others. In contrast, the two survivors from Group II showed a slower rate of recovery and demonstrated some mild to moderate neurological deficits such as hind-limb weakness and decreased vision. These deficits appeared to resolve within one week.

Neurological deficit scores were 0 at days one and two postoperatively for the experimental group (Group I) compared with 1.5±0.5 for the control group (Group II); at one week postoperatively, NDS scores were 0±0 vs. 1.0±1.0 for the two groups respectively.

EXAMPLE 4

Blood samples were collected and analyzed for a wide range of biochemical and hematological parameters prior to, and after exposure to the hypothermic blood substitution procedure. Samples were also collected on days 1, 2 and 3 and weeks 1, 2 and 3, respectively.

Hematocrit, hemoglobin, and red cell counts were slightly suppressed for two weeks postoperatively in all surviving dogs. Platelet counts were decreased postoperatively but were normal by one week later. Prothrombin time was not elevated and fibrinogen was normal except for the immediate post-hypothermia.

All dogs, irrespective of the experimental treatments showed normal electrolyte levels following the procedure. Only magnesium concentrations deviated from normal levels during the immediate postoperative period and these had returned to normal by the first postoperative day. Similarly, serum glucose levels were elevated in the first postoperative samples from animals in both groups, but were in the normal canine range by day 1. Indications of hepato-renal functions, such as blood urea nitrogen (BUN), creatinine and bilirubin all remained within the normal ranges in all dogs throughout the postoperative follow-up. Cholesterol, triglycerides and amylase levels were also normal.

Measurements of enzymes that might reveal any injury in vital tissues such as muscle, liver, heart and brain showed the following changes: Lactate Dehydrogenase (LDH) did not exceed normal values at any point in Group I animals perfused with maintenance solution. However, as shown in FIG. 1, LDH values for dogs perfused with purge solution alone were highly elevated and were significantly greater ($P<0.05$) at each sampling point within the first two postoperative weeks. Other diagnostic enzymes were elevated in animals in both groups, however, the extent of increase in Group I animals perfused with maintenance solution, was generally modest compared with the enormous rises measured in Group II animals perfused with purge solution alone. The results are shown in Table 2.

Serum levels of creatinine kinase (CK) and its isozymes are used clinically as sensitive indicators of injury and disease in specific organs and tissues. FIGS. 2a–2d show that increase in the levels of CK and its isozymes for skeletal muscle (CK-MM), brain (CK-BB) and heart (CK-MB) were transiently and moderately elevated in Group I animals compared with the huge and more prolonged increases recorded in the surviving control animals of Group II.

Figure 3:
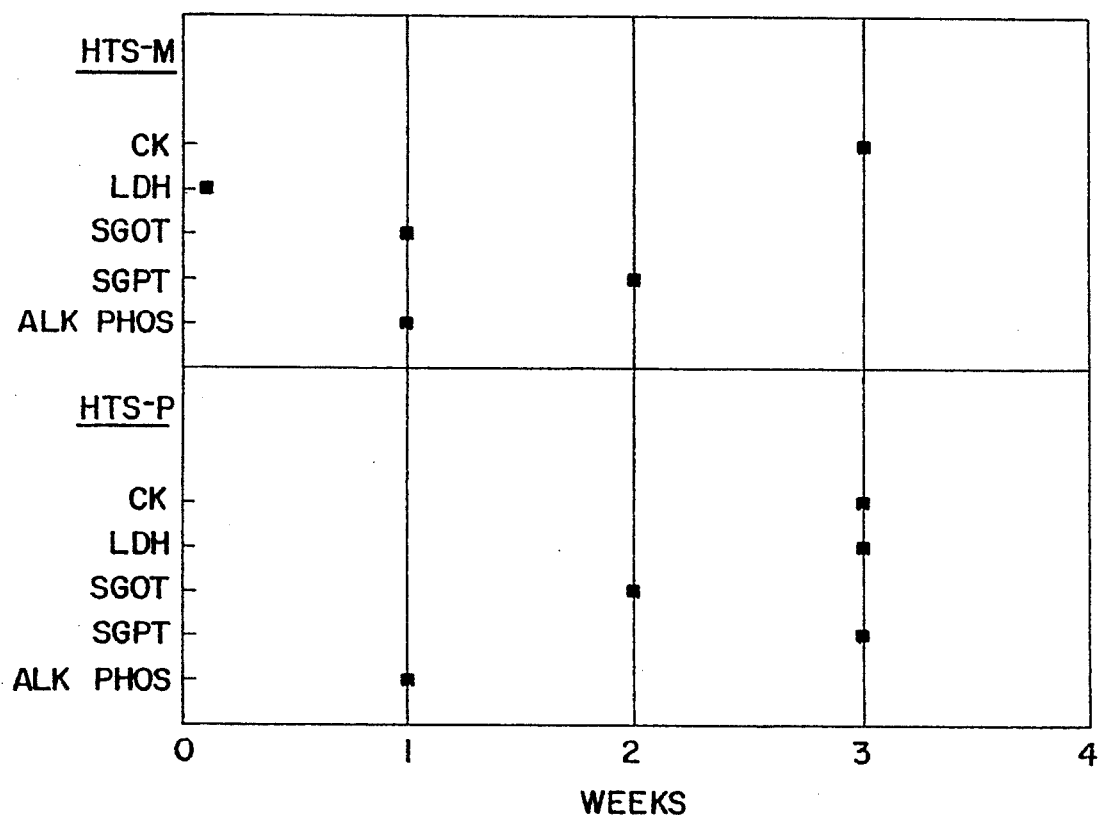
FIG. 3 is a graphic representation showing the time for normalization of serum enzyme levels for experimental (HTS-P/HTS-M) and control (HTS-P) animals.

The transient nature of increased serum enzymes in the group I animals compared with the pair of group II survivors is illustrated in FIG. 3. Three of the five enzymes measured had returned to normal levels within one week in the group I animals whereas, only alkaline phosphatase had returned to normal in the same period in group II animals. Moreover, only creatinine kinase remained elevated for up to three weeks in Group I whereas, LDH, SGPT and CK remained higher than the normal range for up to three weeks in Group II. Although CK was the only enzyme to remain above normal levels for more than two weeks post-operatively in the group I animals, the actual extent of elevation was very modest compared with the values for surviving control dogs (group II). Table 2 shows that after seven days, total CK was only 1.8±0.5 times greater than pre-op values in group I animals compared with 6.3±2.5 times higher for the controls (group II). Measurements of the CK isozymes revealed that the mean proportional increases in isozyme release was greater for muscle (CK-MM) and heart (CK-MB) than for brain (CK-BB), which showed only a 3-fold increase on day 1 in group I animals. For the control dogs the mean proportional increase in the brain fraction of serum CK was an order of magnitude greater at day 1. Table 2 also shows that heart and skeletal muscle fractions of CK had returned to pre-op levels within 1 week in the group I animals but remained 4–5 fold higher in the control group.

The faster return to normalcy of tissue biochemistry in Group I, as judged by the measured release of a variety of enzymes, correlates with the noticeably quicker neurological recovery of dogs in group I compared with the revived dogs from the control group.

The two surviving control dogs and one of the long-term surviving dogs from the experimental group were sacrificed at 18, 26 and 76 weeks, respectively. Gross postmortem examination revealed no abnormalities in any of the tissues from dogs in either group except in the hearts from the control animals. In both cases, severe scar tissue was prevalent in the right and left ventricles indicative of repairs from multiple myocardial infarcts. Histopathology showed multiple microscopic lesions associated with thrombosis of the endocardium. These observations are consistent with the enzyme profiles which showed that serum CK-MB (heart fraction) was only marginally elevated in group I dogs and normal values were recorded within 1 week postoperatively. This contrasts markedly with the surviving controls in which there was 146±19 fold increase in CK-MB on the first day and a persistent 5-fold elevation after 1 week.

function) after storage for one week at 4° C. (n=3) as compared to (c) fresh control tissue (HEM).

Figure 4A:
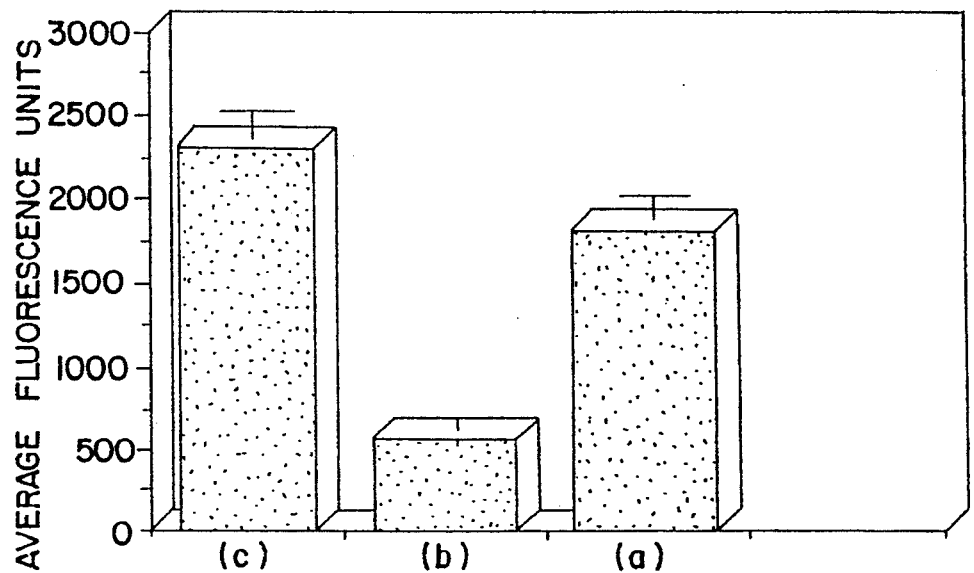
FIG. 4A is a bar graph of plasma membrane integrity i terms of average fluorescence units for Human Epidermal Model (HEM) skin stored for one week at 4° C. in (a) HTS-M, (b) culture medium, KGM, or (c) fresh control sample HEM.

From FIG. 4A it is seen that plasma membrane integrity of skin keratinocytes in the HEM was severely compromised after storage in KGM. However, the retention of the fluorescent probes in the HTS-M stored HEM is not significantly different from the fresh control tissue.

Figure 4B:
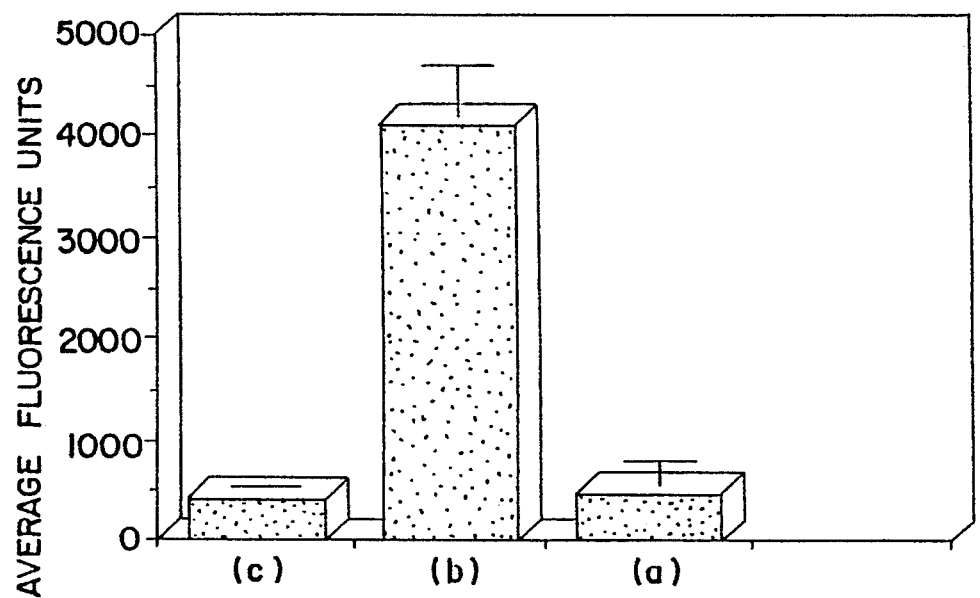
FIG. 4B is a bar graph of epidermal barrier function of HEM stored for one week in (a) HTS-M, (b) KGM, or (c) fresh control sample HEM.

Similarly, from FIG. 4B it is seen that the human epidermal layer of HEM stored in KGM was adversely compromised (high permeability of sodium fluoscein across the tissue layer into the measuring chamber). In sharp contrast, HEM stored in HTS-M retained a bar-

TABLE 2

Proportional increase in post-operative serum enzyme levels relative to pre-operative levels[1]

| | CK | CKBB | CKMB | CKMM | SGOT | SGPT | LDH | ALKPHOS |
|---|---|---|---|---|---|---|---|---|
| | | | | 1 DAY POST-OP | | | | |
| Maintenance Solution (n = 11) | 47.2 ± 13.9 | 3.0 ± 0.7 | 9.4 ± 2.6 | 73.2 ± 25.3 | 23.2 ± 4.5 | 3.5 ± 0.4 | 4.1 ± 0.8 | 4.8 ± 0.5 |
| Purge Solution (n = 2) | 746.1 ± 283.1 | 30.1 ± 5.3 | 146.3 ± 18.6 | 1075.3 ± 520.8 | 308.5 ± 192.1 | 11.8 ± 5.2 | 38.0 ± 5.5 | 2.3 ± 0.4 |
| | | | | 7 DAYS POST-OP | | | | |
| Maintenance Solution (n = 8) | 1.8 ± 0.5 | 4.3 ± 1.9 | 1.0 ± 0.1 | 1.2 ± 0.3 | 1.7 ± 0.2 | 2.3 ± 0.4 | 3.6 ± 1.1 | 2.7 ± 0.2 |
| Purge Solution (n = 2) | 6.3 ± 2.5 | 14.7 ± 0.3 | 5.1 ± 2.2 | 4.2 ± 2.1 | 6.1 ± 3.5 | 8.0 ± 2.0 | 16.5 ± 0.1 | 2.7 ± 0.2 |

Notes and Key
[1]Mean Proportional Increase (± SEM)
CK = Creatine Kinase
CKBB = Creatine Kinase Isozyme (Brain Fraction)
CKMB = Creatine Kinase Isozyme (Heart Fraction)
CK-MM = Creatine Kinase Isozyme (Muscle Fraction)
SGOT = Serum Glutamate-Oxaloacetate Transaminase
SGPT = Serum Glutamate-Pyruviate Transaminase
LDH = Lactate Dehydrogenase
ALKPHOS = Alkaline Phosphatase

EXAMPLE 5

This example illustrates the use of the cell-free hypothermic blood substitute (maintenance) solution for preservation of human skin. The human skin was grown in culture according to techniques which are known in the art and described in the literature. Such skin is known in the art as Human Epidermal Model (HEM) skin. In this example the HEM skin was prepared by Dr. Rob Van Buskirk at the State University of New York.

HEM were stored for one week at 4° C. in (a) HTS-M, or (b) a conventional culture medium, namely keratinocyte growth medium (KGM).

Typically, storage of HEM under refrigerated conditions in a conventional culture medium results in cellular debris from the dermis being presented in the surrounding culture medium within the first seven days. The epidermis shrinks after only two days at 4° C. Epidermal cells become pyknotic, and after longer periods of storage (3 weeks) the epidermis becomes completely separated from the dermis.

In this experiment, plasma membrane integrity was examined by labelling the HEM with Calcein-AM after warming. The in situ level of Calcein was measured using a fluorescent probe (fluorescence multiple end point assay). The results are shown in FIG. 4A for (a) storage in HTS-M, (b) storage in KGM, or (c) a fresh control tissue (HEM). The bars above each column represent the standard errors of the mean, n=3. FIG. 4B illustrates the effect of storage in each of the media (a) and (b) on epidermal permeability (epidermal barrier rier function that was equivalent to fresh control tissue.

Some tissues were shipped and then stored for several days to evaluate the ability of the hypothermically preserved cells to remain viable after transport. These cells also maintained integrity after rewarming. The HEM were prepared for transmission electron microscopy following fluorescence assays. Micrographs of the HEM stored for one week in KGM medium showed dramatic ultrastructural changes compared to the control (fresh) samples. Although the apical surface remained intact, there were large intercellular gaps between adjacent cells. Keratin filaments were highly disorganized at the basal surface, empty vesicles and lipid vesicles were apparent, and the basal membrane was irregular.

In contrast, for the HEM which was stored in HTS-M for one week at 4° C., the micrographs depict that the apical surface still demonstrated microvilli. Compared to samples stored in KGM media, there were fewer spaces between the apical cells. Desmosomes were present between adjacent cells. Keratin filaments were still organized in parallel arrays near the perimeters of the cells. The basal surface of HTS-M stored HEM demonstrated numerous vesicles, an occasional lipid vesicle, and keratin filaments present in parallel bundles. In summary, cells protected by HTS-M maintained viability.

EXAMPLE 6

This example illustrates the use of the invention blood substitute solution in multi-organ retrieval from a brain dead organ donor (cadaver).

The brain dead organ is ventilated with 100% oxygen. A femoral or right radial artery is catheterized for arterial pressure determination and a femoral or radial vein will be catheterized for drug delivery. 25,000 units of heparin will be administered through the venous catheter. A S-G catheter is introduced into a terminal branch of the pulmonary artery via a jugular vein to determine pulmonary arterial wedge pressure. The body of the organ donor will be lowered into a tub of crushed ice and its temperature is lowered to 30 degrees C. At 30 degrees C. the right or left carotid or femoral artery and jugular or femoral vein are cannulated and the cannulate are connected to a cardiopulmonary bypass circuit containing a roller pump or other appropriate pumping means and an oxygenator (with a built-in heat exchanger) of the hollow fiber, membrane or bubble type. The ventilator stroke volume is reduced as the temperature declines. As wedge pressure increases, blood is withdrawn from the femoral artery.

The temperature will then be lowered further by ice-water bath until 25 degrees C., and the circulation then placed on by-pass with the blood being hemodiluted by addition of the invention purge solution, e.g. HTS-P until the hematocrit is reduced to 50% of normal. The lungs will be placed on 7 mm Hg PEEP. The pulmonary wedge pressure will be maintained below 15 mm Hg. The patient is then further chilled to 20 degrees C. or when cardiac fibrillation occurs. At this time an amount of HTS-P equal to the estimated blood volume and that in the by-pass circuit (defined here as the system volume) is added. This is followed by two volumes of maintenance solution, e.g. HTS-M. The chilled oxygenated HTS-M will then be circulated throughout the circuit until temperature close to the ice point are reached. A system volume of HTS-M will be flushed through the circuit every 20 minutes to 180 minutes and the effluent drained. pH and blood gases will be monitored before and after each flush. When the organs are needed for transplantation or when the temperature reaches the ice-point, the HTS-M is replaced by a system volume of HTS-P. At this time organs will be removed for transplantation in the order that they are needed. This method will allow organs to be retrieved and stored for extended periods, e.g. 8 to 48 hours or more, with no warm ischemia time.

What is claimed is:

1. A cell-free hypothermic blood substitute comprising
   (1) an aqueous solution of electrolytes comprising potassium ions at a concentration range of from 35 to 45 mM, sodium ions at a concentration range of from 80 to 120 mM, magnesium ions at a concentration range of from 2 to 10 mM, and calcium ions at a concentration range of from 0.01 to 0.1 mM,
   (2) a macromolecular oncotic agent having a size sufficiently large to limit escape from the circulation system and effective to maintain oncotic pressure equivalent to that of blood plasma and selected from the group consisting of human serum albumin, polysaccharide and colloidal starch,
   (3) a biological pH buffer effective under physiological and hypothermic conditions,
   (4) a nutritive effective amount of at least one simple nutritive sugar,
   (5) an impermeant and hydroxyl radical scavenging effective amount of mannitol,
   (6) an impermeant anion impermeable to cell membranes and effective to counteract cell swelling during cold exposure, said impermeant ion being at least one member selected from the group consisting of lactobionate, gluconate, citrate and glycerophosphate, and
   (7) a substrate effective for the regeneration of ATP said substrate being at least one member selected from the group consisting of adenosine, fructose, ribose and adenine, and may additionally contain,
   (8) glutathione.

2. The blood substitute according to claim 1 wherein the macromolecular oncotic agent comprises an impermeant polysaccharide.

3. The blood substitute according to claim 2 wherein the impermeant polysaccharide is Dextran 40.

4. The blood substitute according to claim 2 wherein the impermeant polysaccharide is Dextran 70.

5. The blood substitute according to claim 1 wherein said solution further comprises an inhibitor of xanthine oxidase and a 5' nucleotidase inhibitor.

6. The blood substitute according to claim 1 wherein said solution further comprises an iron-chelating agent.

7. The blood substitute according to claim 1 wherein said solution further comprises at least one fast channel blocker.

8. The blood substitute according to claim 7 wherein said at least one fast channel blocker is lidocaine.

9. The blood substitute according to claim 1 wherein said impermeant anion (6) is a lactobionate salt in a concentration of about 100 mM.

10. The blood substitute according to claim 1 wherein said solution further comprises buffering amounts of $H_2PO_4^-$ and $HCO_3^=$.

11. The blood substitute according to claim 1 wherein glutathione is present.

12. The blood substitute of claim 1 which comprises:
    (1) said aqueous solution of electrolytes;
    (2) an amount effective to maintain oncotic pressure equivalent to that of blood plasma of said colloidal macromolecular oncotic agent selected from the group consisting of human serum albumin, polysaccharide having a molecular weight in the range of from about 30,000 to about 70,000, and artificial colloidal waxy starch;
    (3) said biological pH buffer;
    (4) from about 1 mM to about 1M of said nutritive sugar;
    (5) from about 10 mM to about 20 mM of mannitol;
    (6) an amount effective to counteract cell swelling during cold exposure of said impermeant anion;
    (7) from about 0.5 mM to about 2 mM of said ATP substrate; and
    (8) up to about 5 mM of glutathione.

13. The blood substitute of claim 12 which comprises:
    (1) said aqueous solution of electrolytes;
    (2) an amount of impermeant polysaccharide having a molecular weight in the range of from about 30,000 to about 70,000, said amount being sufficient to provide a colloid pressure approximating that of normal human serum;
    (3) said biological pH buffer;
    (4) from about 1 mM to about 10 mM of glucose;
    (5) from about 10 mM to about 20 mM of mannitol;

(6) from about 80 mM to about 120 mM of lactobionate;
(7) from about 0.5 mM to about 2 mM of adenosine; and
(8) from about 1 mM to about 5 mM of glutathione; said composition having an osmolality in the range of from about to 370 milliosmoles.

14. The blood substitute of claim 13 wherein the concentration of calcium ions in said aqueous solution of electrolytes is from about 0.01 to 0.07 mM, and the concentration of magnesium ions is from about 2.5 to 7.5 mM, said aqueous solution of electrolytes further comprising chloride ions at a concentration in the range of about 2.5 to 7.0 mM.

15. A method for preserving an organ for transplantation comprising infusing the organ to be transplanted with a preservation effective amount of an intracellular maintenance solutions comprising
(1) an aqueous solution of electrolytes comprising potassium ions at a concentration range of from 35 to 45 mM, sodium ions at a concentration range of from 80 to 120 mM, magnesium ions at a concentration range of from 2 to 10 mM, and calcium ions at a concentration range of from 0.01 to 0.1 mM,
(2) a macromolecular oncotic agent having a size sufficiently large to limit escape from the circulation system and effective to maintain oncotic pressure equivalent to that of blood plasma and selected from the group consisting of human serum albumin, polysaccharide and colloidal starch,
(3) a biological pH buffer effective under physiological and hypothermic conditions,
(4) a nutritive effective amount of at least one simple nutritive sugar,
(5) an impermeant and hydroxyl radical scavenging effective amount of mannitol,
(6) an impermeant anion impermeable to cell membranes and effective to counteract cell swelling during cold exposure, said impermeant ion being at least one member selected from the group consisting of lactobionate, gluconate, citrate and glycerophosphate, and
(7) a substrate effective for the regeneration of ATP said substrate being at least one member selected from the group consisting of adenosine, fructose, ribose and adenine, and may additionally contain,
(8) glutathione.

16. The method for preserving an organ for transplantation according to claim 15 wherein the organ is preserved with the intracellular maintenance solution at a temperature of from about 2° C. to about 12° C.

17. The method for preserving an organ for transplantation according to claim 15 wherein the organ is a heart.

18. The method for preserving an organ for transplantation according to claim 15 wherein the organ is human skin or synthetic human epidermal skin.

19. The method for preserving an organ for transplantation according to claim 15 wherein the organ is a cornea.

* * * * *